(12) United States Patent
Amstutz

(10) Patent No.: US 10,511,813 B1
(45) Date of Patent: Dec. 17, 2019

(54) SYSTEMS, DEVICES, AND/OR METHODS FOR LOGGING WRITING ACTIVITIES

(71) Applicant: Logan Amstutz, Hart, MI (US)

(72) Inventor: Logan Amstutz, Hart, MI (US)

(*) Notice: Subject to any disclaimer, the term of this patent is extended or adjusted under 35 U.S.C. 154(b) by 0 days.

(21) Appl. No.: 16/194,370

(22) Filed: Nov. 18, 2018

(51) Int. Cl.
*H04N 7/18* (2006.01)
*A61B 5/11* (2006.01)
*A61B 5/16* (2006.01)
*G06K 9/00* (2006.01)

(52) U.S. Cl.
CPC .......... *H04N 7/185* (2013.01); *A61B 5/1128* (2013.01); *A61B 5/11* (2013.01); *A61B 5/16* (2013.01); *G06K 9/00402* (2013.01)

(58) Field of Classification Search
None
See application file for complete search history.

(56) References Cited

U.S. PATENT DOCUMENTS

| | | | |
|---|---|---|---|
| 2008/0088604 A1* | 4/2008 | Cohen | G06F 3/002 345/179 |
| 2016/0062118 A1* | 3/2016 | Osterhout | G02B 27/0172 345/8 |
| 2016/0098594 A1* | 4/2016 | Sugiura | G06K 9/00422 382/189 |
| 2017/0231527 A1* | 8/2017 | Jaeger | A61B 5/11 702/141 |

* cited by examiner

*Primary Examiner* — Fernando Alcon
(74) *Attorney, Agent, or Firm* — Dale Jensen, PLC; Dale Jensen

(57) ABSTRACT

Certain exemplary embodiments can provide a method, which comprises causing an image or video to be transmitted to a database. The image or video is transmitted from a body camera worn by a user. The image or video is linked to detected writing of the user. The writing is detected via a device worn on a hand of the user. The device is worn on the hand of the user and is not comprised by the body camera.

3 Claims, 4 Drawing Sheets

1000

SYSTEMS, DEVICES, AND/OR METHODS FOR LOGGING WRITING ACTIVITIES

BRIEF DESCRIPTION OF THE DRAWINGS

A wide variety of potential practical and useful embodiments will be more readily understood through the following detailed description of certain exemplary embodiments, with reference to the accompanying exemplary drawings in which.

DETAILED DESCRIPTION

Certain exemplary embodiments can provide a method, which comprisesvcausing an image or video to be transmitted to a database. The image or video is transmitted from a body camera worn by a user. The image or video is linked to detected writing of the user. The writing is detected via a device worn on a hand of the user. The device is worn on the hand of the user and is not comprised by the body camera.

Figure 1:
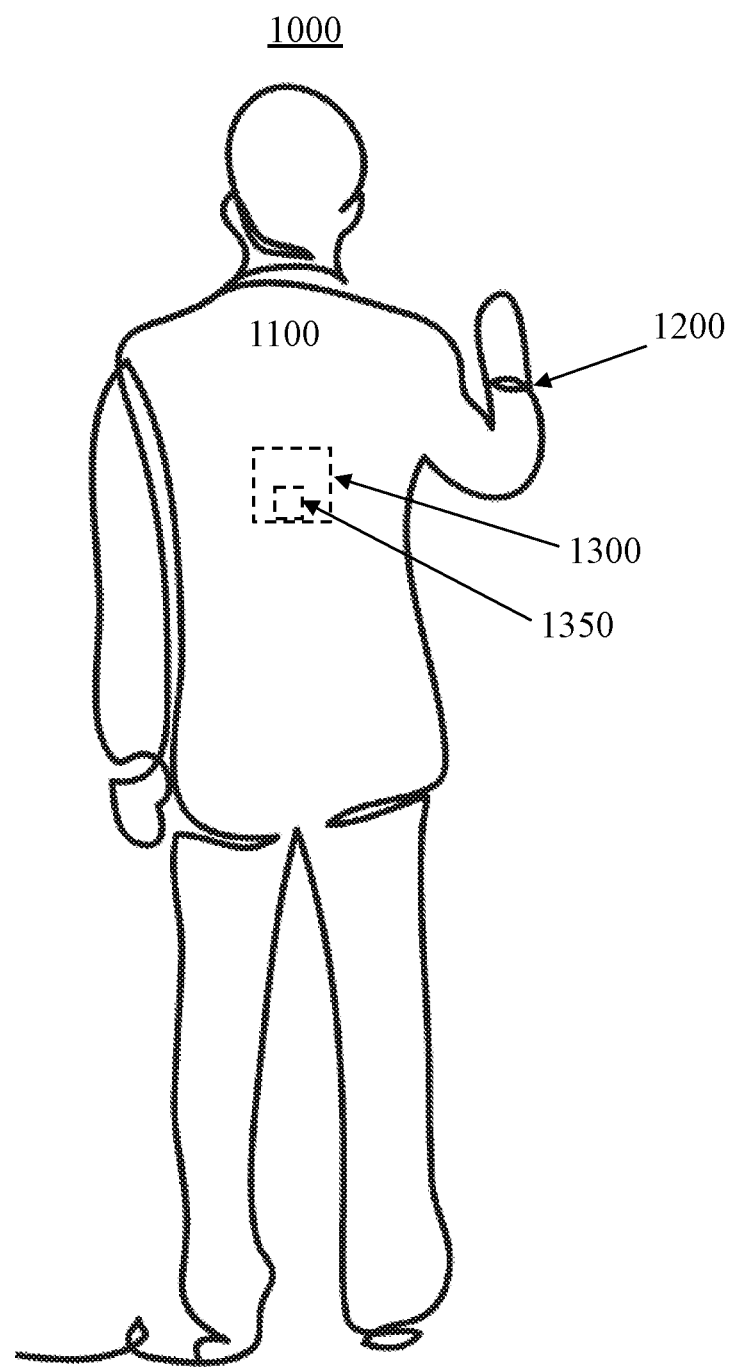
FIG. 1 is a view of an exemplary embodiment of a system 1000.

FIG. 1 is a side view of an exemplary embodiment of a system 1000, which comprises a user 1100 wearing a writing sensor 1200, and a body camera 1300. Body camera 1300 comprises a wireless transceiver. Writing sensor 1200 is illustrated as a device worn on a wrist of a user. In other embodiments, writing sensor 1200 can comprise a camera. Any camera comprised by the system, whether body camera 1300 or the camera comprised by writing sensor 1200 can be constructed to obtain and transmit still images and video streams. Any camera comprised by the system, whether body camera 1300 or the camera comprised by writing sensor 1200 can be constructed to place a date and time stamp on each still image and video stream.

Body camera 1300 takes images and/or videos of both the writing action of user 1100 and visible surroundings of user 1100. User 1100 can direct body camera 1300 in a manner to provide images and/or videos deemed important by user 1100. User 1100 writes thoughts out by hand. In certain exemplary embodiments, the writing can be on a surface that visually shows the writing (e.g., a paper written on by a pen). In other embodiments, the writing can be on a surface that generates an electronic signal indicative of writing, but might not show a visually discernable writing.

In certain exemplary embodiments, the writing information and/or images and/or videos can be provided to a psychiatric professional that examines each. The psychiatric professional can observe the information and can adjust counseling and/or medication responsive to observations made concerning the information.

Figure 2:
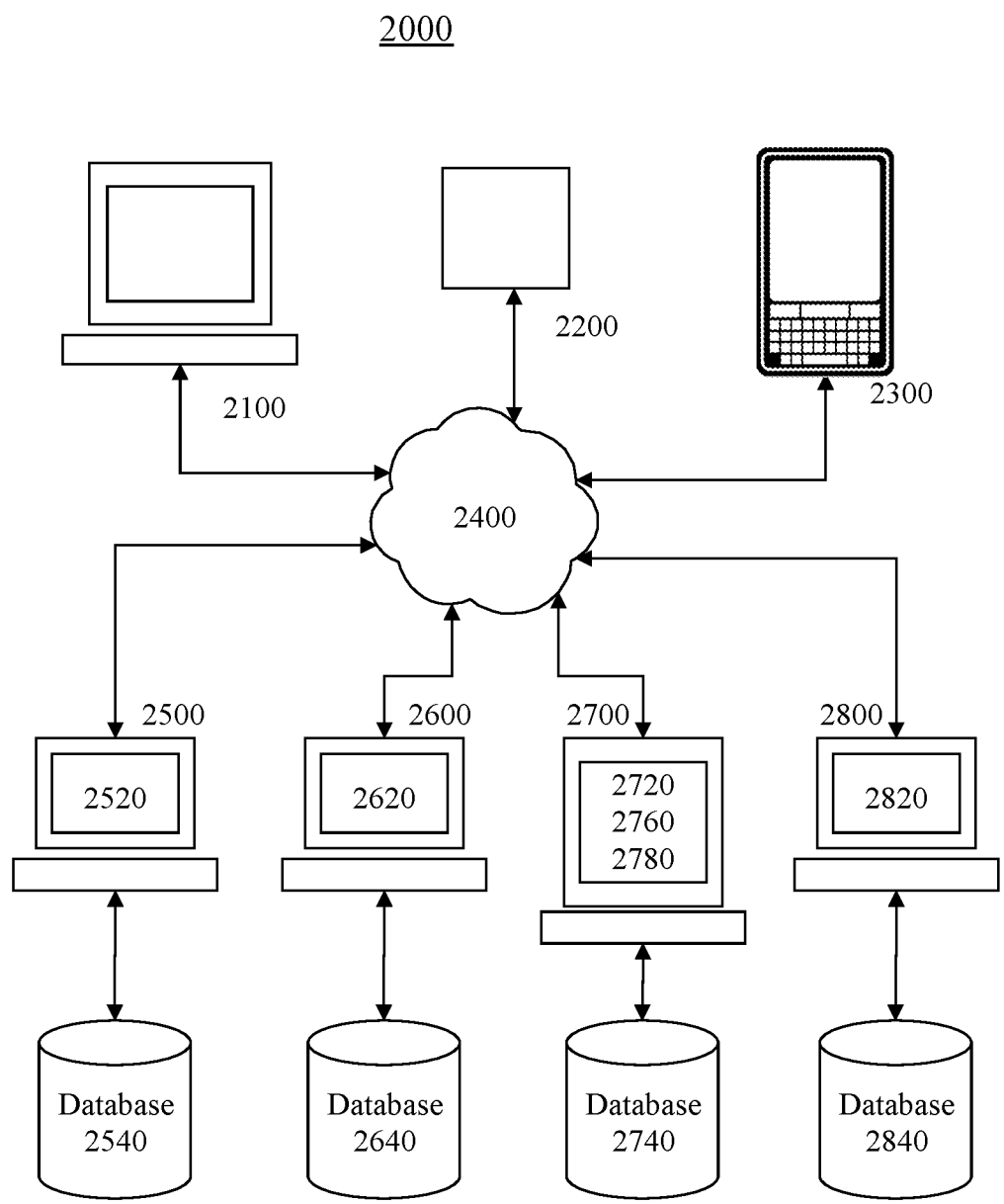
FIG. 2 is a block diagram of an exemplary embodiment of a system 2000.

FIG. 2 is a block diagram of an exemplary embodiment of a system 2000, which can comprise a smartphone 2300, an information device 2100, tablet 2200, a network 2400, a first server 2500, a second server 2600, a third server 2700, and a fourth server 2800. First server 2500 can comprise a first user interface 2520 and can be coupled to a first database 2540. Second server 2600 can comprise a second user interface 2620 and can be coupled to a second database 2640. Third server 2700 can comprise a third user interface 2720, a processor 2760, machine instructions 2780, and can be coupled to a third database 2740. Fourth server 2800 can comprise a fourth user interface 2820 and can be coupled to a fourth database 2840. Any of the methods and/or steps thereof can be carried out in whole or in part by tablet 2200, smartphone 2300, information device 2100 and/or first server 2500. Second server 2600, third server 2700, and/or fourth server 2800 can each be associated with implementation of a system via which rides are provided to customers. In certain exemplary embodiments, system 2000 can be used to implement one or more methods disclosed herein.

Figure 3:
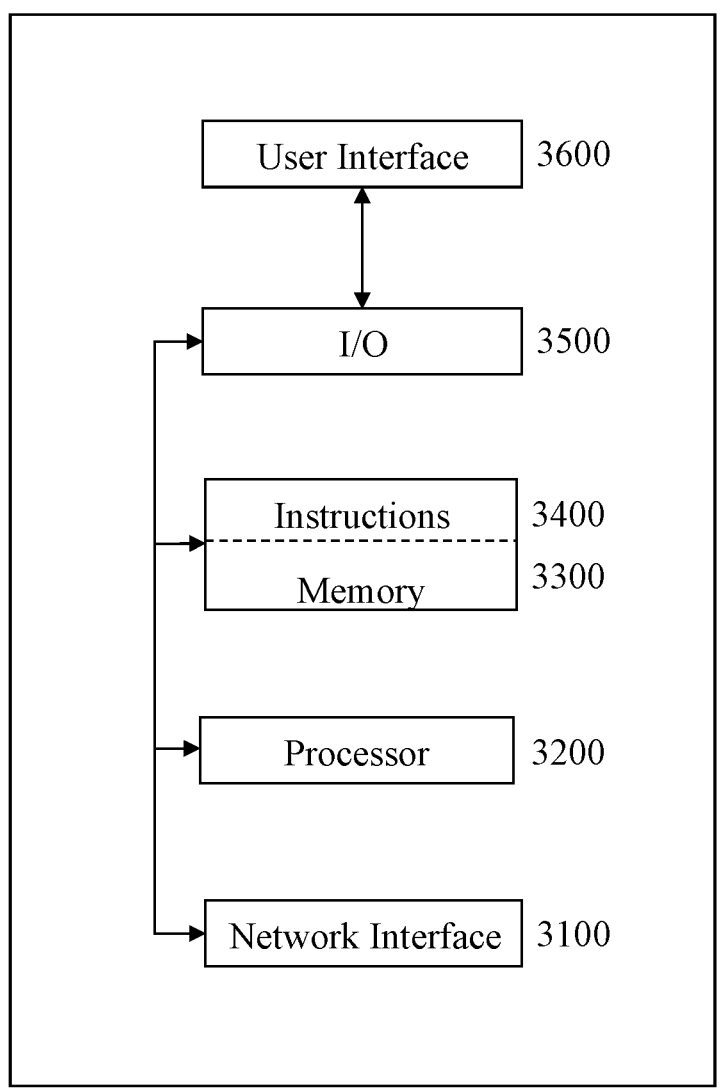
FIG. 3 is a block diagram of an exemplary embodiment of an information device 3000.

FIG. 3 is a block diagram of an exemplary embodiment of an information device 3000, which in certain operative embodiments can comprise, for example, first server 2500 and information device 2100, of FIG. 2. Information device 3000 can comprise any of numerous circuits and/or components, such as for example, one or more network interfaces 3100, one or more processors 3200, one or more memories 3300 containing instructions 3400, one or more input/output (I/O) devices 3500, and/or one or more user interfaces 3600 coupled to one or more I/O devices 3500, etc.

In certain exemplary embodiments, via one or more user interfaces 3600, such as a graphical user interface, a user can view a rendering of information related to writing, images, and/or video of a user.

Figure 4:
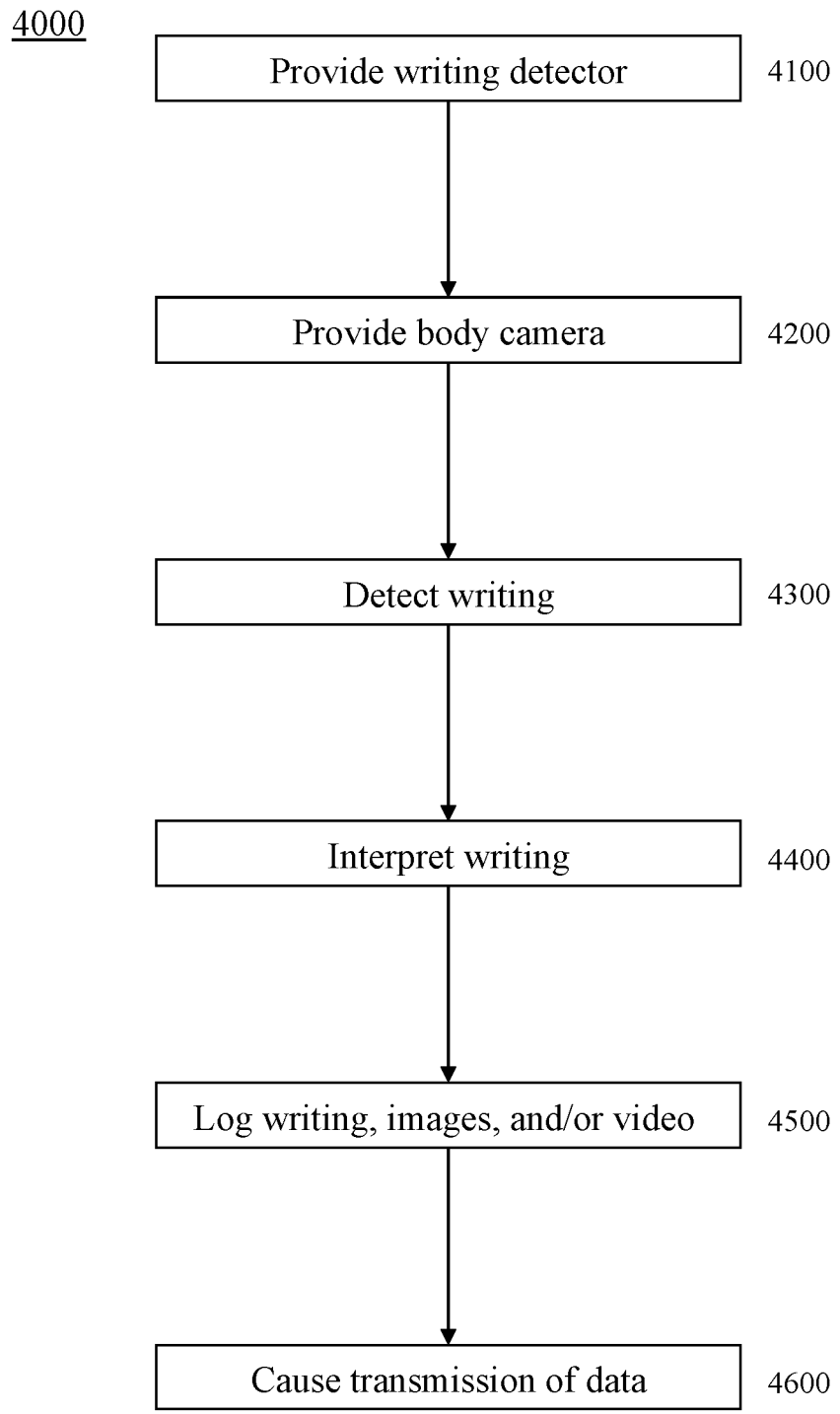
FIG. 4 is a flowchart of an exemplary embodiment of a method 4000.

FIG. 4 is a flowchart of an exemplary embodiment of a method 4000. At activity 4100, a writing detector can be provided to a user. At activity 4200, a body camera can be provided to the user. At activity 4300, writing can be detected via the writing detector. At activity 4400, the writing can be automatically interpreted via machine instructions that convert writing to character recognized text. At activity 4500, certain exemplary embodiments can cause writing, images and/or videos to a log.

At activity 4600, certain exemplary embodiments can cause writing, image, and/or video data can be transmitted. Certain exemplary embodiments can cause an image or video to be transmitted to a database. The image or video can be transmitted from a body camera worn by a user. The image or video can be linked to detected writing of the user. The writing can be detected via a device worn on a hand of the user. The device can be worn on the hand of the user is not comprised by the body camera. The writing can be automatically analyzed and information of the writing is linked to the image or video transmitted from the body camera worn by the user. The device can comprise a hand camera. An image from the hand camera is automatically transmitted to the database and linked to the image or video transmitted from the body camera. The content of the writing can be automatically detected and transmitted to the database and linked to the image or video transmitted from the body camera

Definitions

When the following terms are used substantively herein, the accompanying definitions apply. These terms and definitions are presented without prejudice, and, consistent with the application, the right to redefine these terms during the prosecution of this application or any application claiming priority hereto is reserved. For the purpose of interpreting a claim of any patent that claims priority hereto, each definition (or redefined term if an original definition was amended during the prosecution of that patent), functions as a clear and unambiguous disavowal of the subject matter outside of that definition.

a—at least one.

activity—an action, act, step, and/or process or portion thereof analyze—evaluate.

and/or—either in conjunction with or in alternative to.

apparatus—an appliance or device for a particular purpose associate—to join, connect together, and/or relate.

automatically—acting or operating in a manner essentially independent of external influence or control. For example, an automatic light switch can turn on upon "seeing" a person in its view, without the person manually operating the light switch.

body—a physical form of a human.

camera—an instrument constructed to record and/or capture still and/or moving images.

can—is capable of, in at least some embodiments.

cause—to produce an effect.

comprising—including but not limited to.

configure—to make suitable or fit for a specific use or situation.

constructed to—made to and/or designed to.

content—information convert—to transform, adapt, and/or change.

create—to bring into being.

data—distinct pieces of information, usually formatted in a special or predetermined way and/or organized to express concepts.

database—a collection of information organized and linked in such a way that a computer program can quickly select desired pieces of data.

define—to establish the outline, form, or structure of detect—to sense or perceive.

determine—to obtain, calculate, decide, deduce, and/or ascertain.

device—a machine, manufacture, and/or collection thereof.

estimate—to calculate and/or determine approximately and/or tentatively.

generate—to create, produce, give rise to, and/or bring into existence.

haptic—involving the human sense of kinesthetic movement and/or the human sense of touch. Among the many potential haptic experiences are numerous sensations, body-positional differences in sensations, and time-based changes in sensations that are perceived at least partially in non-visual, non-audible, and non-olfactory manners, including the experiences of tactile touch (being touched), active touch, grasping, pressure, friction, traction, slip, stretch, force, torque, impact, puncture, vibration, motion, acceleration, jerk, pulse, orientation, limb position, gravity, texture, gap, recess, viscosity, pain, itch, moisture, temperature, thermal conductivity, and thermal capacity.

image—an at least two-dimensional representation of an object and/or phenomenon.

information—data that has been organized to express concepts.

information device—any device capable of processing data and/or information, such as any general purpose and/or special purpose computer, such as a personal computer, workstation, server, minicomputer, mainframe, supercomputer, computer terminal, laptop, wearable computer, and/or Personal Digital Assistant (PDA), mobile terminal, Bluetooth device, communicator, "smart" phone (such as a Treo-like device), messaging service (e.g., Blackberry) receiver, pager, facsimile, cellular telephone, a traditional telephone, telephonic device, a programmed microprocessor or microcontroller and/or peripheral integrated circuit elements, an ASIC or other integrated circuit, a hardware electronic logic circuit such as a discrete element circuit, and/or a programmable logic device such as a PLD, PLA, FPGA, or PAL, or the like, etc. In general any device on which resides a finite state machine capable of implementing at least a portion of a method, structure, and/or or graphical user interface described herein may be used as an information device. An information device can comprise components such as one or more network interfaces, one or more processors, one or more memories containing instructions, and/or one or more input/output (I/O) devices, one or more user interfaces coupled to an I/O device, etc.

initialize—to prepare something for use and/or some future event.

input/output (I/O) device—any sensory-oriented input and/or output device, such as an audio, visual, haptic, olfactory, and/or taste-oriented device, including, for example, a monitor, display, projector, overhead display, keyboard, keypad, mouse, trackball, joystick, gamepad, wheel, touchpad, touch panel, pointing device, microphone, speaker, video camera, camera, scanner, printer, haptic device, vibrator, tactile simulator, and/or tactile pad, potentially including a port to which an I/O device can be attached or connected.

link—to connect via a reference value that enables a program to access a particular piece of data.

machine instructions—directions adapted to cause a machine, such as an information device, to perform one or more particular activities, operations, or functions. The directions, which can sometimes form an entity called a "processor", "kernel", "operating system", "program", "application", "utility", "subroutine", "script", "macro", "file", "project", "module", "library", "class", and/or "object", etc., can be embodied as machine code, source code, object code, compiled code, assembled code, interpretable code, and/or executable code, etc., in hardware, firmware, and/or software.

machine readable medium—a physical structure from which a machine can obtain data and/or information. Examples include a memory, punch cards, etc.

may—is allowed and/or permitted to, in at least some embodiments.

memory device—an apparatus capable of storing analog or digital information, such as instructions and/or data. Examples include a non-volatile memory, volatile memory, Random Access Memory, RAM, Read Only Memory, ROM, flash memory, magnetic media, a hard disk, a floppy disk, a magnetic tape, an optical media, an optical disk, a compact disk, a CD, a digital versatile disk, a DVD, and/or a raid array, etc. The memory device can be coupled to a processor and/or can store instructions adapted to be executed by processor, such as according to an embodiment disclosed herein.

method—a process, procedure, and/or collection of related activities for accomplishing something.

network—a communicatively coupled plurality of nodes. A network can be and/or utilize any of a wide variety of sub-networks, such as a circuit switched, public-switched, packet switched, data, telephone, telecommunications, video distribution, cable, terrestrial, broadcast, satellite, broadband, corporate, global, national, regional, wide area, backbone, packet-switched TCP/IP, Fast Ethernet, Token Ring, public Internet, private, ATM, multi-domain, and/or multi-zone sub-network, one or more Internet service providers, and/or one or more information devices, such as a switch, router, and/or gateway not directly connected to a local area network, etc.

network interface—any device, system, or subsystem capable of coupling an information device to a network. For example, a network interface can be a telephone, cellular phone, cellular modem, telephone data modem, fax modem, wireless transceiver, ethernet card, cable modem, digital subscriber line interface, bridge, hub, router, or other similar device.

plurality—the state of being plural and/or more than one.

predetermined—established in advance.

probability—a quantitative representation of a likelihood of an occurrence.

processor—a device and/or set of machine-readable instructions for performing one or more predetermined tasks. A processor can comprise any one or a combination of hardware, firmware, and/or software. A processor can utilize mechanical, pneumatic, hydraulic, electrical, magnetic, optical, informational, chemical, and/or biological principles, signals, and/or inputs to perform the task(s). In certain embodiments, a processor can act upon information by manipulating, analyzing, modifying, converting, transmitting the information for use by an executable procedure and/or an information device, and/or routing the information to an output device. A processor can function as a central processing unit, local controller, remote controller, parallel controller, and/or distributed controller, etc. Unless stated otherwise, the processor can be a general-purpose device, such as a microcontroller and/or a microprocessor, such the Pentium IV series of microprocessor manufactured by the Intel Corporation of Santa Clara, Calif. In certain embodiments, the processor can be dedicated purpose device, such as an Application Specific Integrated Circuit (ASIC) or a Field Programmable Gate Array (FPGA) that has been designed to implement in its hardware and/or firmware at least a part of an embodiment disclosed herein.

project—to calculate, estimate, or predict.

provide—to furnish, supply, give, and/or make available.

receive—to get as a signal, take, acquire, and/or obtain.

recommend—to suggest, praise, commend, and/or endorse.

render—to make perceptible to a human, for example as data, commands, text, graphics, audio, video, animation, and/or hyperlinks, etc., such as via any visual, audio, and/or haptic means, such as via a display, monitor, electric paper, ocular implant, cochlear implant, speaker, etc.

repeatedly—again and again; repetitively.

request—to express a desire for and/or ask for.

select—to make a choice or selection from alternatives.

set—a related plurality.

signal—information, such as machine instructions for activities and/or one or more letters, words, characters, symbols, signal flags, visual displays, and/or special sounds, etc. having prearranged meaning, encoded as automatically detectable variations in a physical variable, such as a pneumatic, hydraulic, acoustic, fluidic, mechanical, electrical, magnetic, optical, chemical, and/or biological variable, such as power, energy, pressure, flowrate, viscosity, density, torque, impact, force, frequency, phase, voltage, current, resistance, magnetomotive force, magnetic field intensity, magnetic field flux, magnetic flux density, reluctance, permeability, index of refraction, optical wavelength, polarization, reflectance, transmittance, phase shift, concentration, and/or temperature, etc. Depending on the context, a signal and/or the information encoded therein can be synchronous, asynchronous, hard real-time, soft real-time, non-real time, continuously generated, continuously varying, analog, discretely generated, discretely varying, quantized, digital, broadcast, multicast, unicast, transmitted, conveyed, received, continuously measured, discretely measured, processed, encoded, encrypted, multiplexed, modulated, spread, de-spread, demodulated, detected, de-multiplexed, decrypted, and/or decoded, etc.

store—to place, hold, and/or retain data, typically in a memory.

substantially—to a great extent or degree.

system—a collection of mechanisms, devices, machines, articles of manufacture, processes, data, and/or instructions, the collection designed to perform one or more specific functions.

transmit—to send as a signal, provide, furnish, and/or supply.

user interface—any device for rendering information to a user and/or requesting information from the user. A user interface includes at least one of textual, graphical, audio, video, animation, and/or haptic elements. A textual element can be provided, for example, by a printer, monitor, display, projector, etc. A graphical element can be provided, for example, via a monitor, display, projector, and/or visual indication device, such as a light, flag, beacon, etc. An audio element can be provided, for example, via a speaker, microphone, and/or other sound generating and/or receiving device. A video element or animation element can be provided, for example, via a monitor, display, projector, and/or other visual device. A haptic element can be provided, for example, via a very low frequency speaker, vibrator, tactile stimulator, tactile pad, simulator, keyboard, keypad, mouse, trackball, joystick, gamepad, wheel, touchpad, touch panel, pointing device, and/or other haptic device, etc. A user interface can include one or more textual elements such as, for example, one or more letters, number, symbols, etc. A user interface can include one or more graphical elements such as, for example, an image, photograph, drawing, icon, window, title bar, panel, sheet, tab, drawer, matrix, table, form, calendar, outline view, frame, dialog box, static text, text box, list, pick list, pop-up list, pull-down list, menu, tool bar, dock, check box, radio button, hyperlink, browser, button, control, palette, preview panel, color wheel, dial, slider, scroll bar, cursor, status bar, stepper, and/or progress indicator, etc. A textual and/or graphical element can be used for selecting, programming, adjusting, changing, specifying, etc. an appearance, background color, background style, border style, border thickness, foreground color, font, font style, font size, alignment, line spacing, indent, maximum data length, validation, query, cursor type, pointer type, autosizing, position, and/or dimension, etc. A user interface can include one or more audio elements such as, for example, a volume control, pitch control, speed control, voice selector, and/or one or more elements for controlling audio play, speed, pause, fast forward, reverse, etc. A user interface can include one or more video elements such as, for example, elements controlling video play, speed, pause, fast forward, reverse, zoom-in, zoom-out, rotate, and/or tilt, etc. A user interface can include one or more animation elements such as, for example, elements controlling animation play, pause, fast forward, reverse, zoom-in, zoom-out, rotate, tilt, color, intensity, speed, frequency, appearance, etc. A user interface can include one or more haptic elements such as, for example, elements utilizing tactile stimulus, force, pressure, vibration, motion, displacement, temperature, etc.

video—a sequential set of images that, when rendered, can be seen by a human or animal and that, when rendered sequentially at a determined rate, appear to a human as if one or more things are moving.

via—by way of and/or utilizing.

weight—a value indicative of importance.

worn—to have on a body of a person.

writing—signs and/or symbols embodied on a physical medium.

Note

Still other substantially and specifically practical and useful embodiments will become readily apparent to those skilled in this art from reading the above-recited and/or herein-included detailed description and/or drawings of certain exemplary embodiments. It should be understood that numerous variations, modifications, and additional embodiments are possible, and accordingly, all such variations, modifications, and embodiments are to be regarded as being within the scope of this application.

Thus, regardless of the content of any portion (e.g., title, field, background, summary, description, abstract, drawing figure, etc.) of this application, unless clearly specified to the contrary, such as via explicit definition, assertion, or argument, with respect to any claim, whether of this application and/or any claim of any application claiming priority hereto, and whether originally presented or otherwise:

there is no requirement for the inclusion of any particular described or illustrated characteristic, function, activity, or element, any particular sequence of activities, or any particular interrelationship of elements;

no characteristic, function, activity, or element is "essential";

any elements can be integrated, segregated, and/or duplicated;

any activity can be repeated, any activity can be performed by multiple entities, and/or any activity can be performed in multiple jurisdictions; and any activity or element can be specifically excluded, the sequence of activities can vary, and/or the interrelationship of elements can vary.

Moreover, when any number or range is described herein, unless clearly stated otherwise, that number or range is approximate. When any range is described herein, unless clearly stated otherwise, that range includes all values therein and all subranges therein. For example, if a range of 1 to 10 is described, that range includes all values therebetween, such as for example, 1.1, 2.5, 3.335, 5, 6.179, 8.9999, etc., and includes all subranges therebetween, such as for example, 1 to 3.65, 2.8 to 8.14, 1.93 to 9, etc.

When any claim element is followed by a drawing element number, that drawing element number is exemplary and non-limiting on claim scope. No claim of this application is intended to invoke paragraph six of 35 USC 112 unless the precise phrase "means for" is followed by a gerund.

Any information in any material (e.g., a United States patent, United States patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such material is specifically not incorporated by reference herein.

Accordingly, every portion (e.g., title, field, background, summary, description, abstract, drawing figure, etc.) of this application, other than the claims themselves, is to be regarded as illustrative in nature, and not as restrictive, and the scope of subject matter protected by any patent that issues based on this application is defined only by the claims of that patent.

What is claimed is:

1. A method comprising:
   causing an image or video to be transmitted to a database, the image or video transmitted from a body camera worn by a user, the image or video linked to detected writing of the user, the writing detected via a device worn on a hand of the user, the device worn on the hand of the user not comprised by the body camera, wherein the writing is automatically analyzed and information of the writing is linked to the image or video transmitted from the body camera worn by the user.

2. The method of claim 1, wherein:
   the device comprises a hand camera and an image from the hand camera is automatically transmitted to the database and linked to the image or video transmitted from the body camera.

3. The method of claim 1, wherein:
   content of the writing is automatically detected and transmitted to the database and linked to the image or video transmitted from the body camera.

* * * * *